(12) United States Patent
Bostick et al.

(10) Patent No.: US 11,029,834 B2
(45) Date of Patent: Jun. 8, 2021

(54) UTILIZING BIOMETRIC FEEDBACK TO ALLOW USERS TO SCROLL CONTENT INTO A VIEWABLE DISPLAY AREA

(71) Applicant: International Business Machines Corporation, Armonk, NY (US)

(72) Inventors: James E. Bostick, Cedar Park, TX (US); John M. Ganci, Jr., Cary, NC (US); Martin G. Keen, Cary, NC (US); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 169 days.

(21) Appl. No.: 15/848,677

(22) Filed: Dec. 20, 2017

(65) Prior Publication Data

US 2019/0187870 A1 Jun. 20, 2019

(51) Int. Cl.
*G06F 3/048* (2013.01)
*G06F 3/0485* (2013.01)
(Continued)

(52) U.S. Cl.
CPC ............ *G06F 3/0485* (2013.01); *G06F 3/015* (2013.01); *G06F 3/04886* (2013.01); *G06F 3/167* (2013.01); *G06K 9/00302* (2013.01); *G06K 9/00335* (2013.01); *G06N 20/00* (2019.01); *A61F 4/00* (2013.01); *G06F 3/012* (2013.01);
(Continued)

(58) Field of Classification Search
CPC ......... G06K 9/300302; G06K 9/00335; G06K 2009/00939; G06K 9/00302; G06F 3/0485; G06F 3/167; G06F 21/32; G06F 2203/011; G06F 3/015; G06F 3/04886; G06F 3/012;
(Continued)

(56) References Cited

U.S. PATENT DOCUMENTS

| 6,067,069 A * | 5/2000 | Krause .................. G06F 3/0481 345/685 |
| 6,603,491 B2 * | 8/2003 | Lemelson ............... G06F 3/013 715/784 |

(Continued)

OTHER PUBLICATIONS

Santos, Samsung Patents Smart Contact Lenses with a Built-In Camera, Futurism, Apr. 6, 2016, https://futurism.com/samsung-patents-smart-contact-lenses-built-camera/, pp. 1-2.

*Primary Examiner* — Jennifer E Nichols
(74) *Attorney, Agent, or Firm* — Will Stock; Edell, Shapiro & Finnan, LLC (57) ABSTRACT

Systems and methods are provided for displaying visual content on an electronic device to a user. In some aspects, a viewable display area on a display of the device is determined, the viewable display area representing the portion of the display that the user is capable of seeing. Biometric data representing a state of the user is obtained from biometric device(s). Each state is mapped to one or more predefined control functions, the control functions determining the scrolling direction and scrolling speed of text through the viewable display area of the electronic device. A control function is selected based on a current state of the user, and the selected control function is used to control scrolling of visual content in real time or near real time. The system comprises a machine learning system to provide advanced adaptive capabilities.

19 Claims, 7 Drawing Sheets

(51) Int. Cl.
*G06F 3/16* (2006.01)
*G06K 9/00* (2006.01)
*G06N 20/00* (2019.01)
*G06F 3/01* (2006.01)
*G06F 3/0488* (2013.01)
*G10L 25/63* (2013.01)
*A61F 4/00* (2006.01)

(52) U.S. Cl.
CPC .............. *G06F 2203/011* (2013.01); *G06K 2009/00939* (2013.01); *G10L 25/63* (2013.01)

(58) Field of Classification Search
CPC .......... G06F 3/013; G06N 20/00; A61F 4/00; G10L 25/63
See application file for complete search history.

(56) References Cited

U.S. PATENT DOCUMENTS

| | | | |
|---|---|---|---|
| 6,886,137 B2* | 4/2005 | Peck | G06F 3/013 345/158 |
| 7,081,905 B1* | 7/2006 | Raghunath | G06F 1/163 345/684 |
| 8,885,882 B1 | 11/2014 | Yin et al. | |
| 8,913,004 B1* | 12/2014 | Bozarth | G09G 5/006 345/156 |
| 8,957,847 B1* | 2/2015 | Karakotsios | G06F 3/0484 345/156 |
| 9,020,825 B1* | 4/2015 | Garber | G06F 3/0485 704/275 |
| 9,110,500 B2* | 8/2015 | Bonnat | G06F 3/0485 |
| 9,182,819 B2 | 11/2015 | Strupczewski et al. | |
| 9,189,064 B2* | 11/2015 | Chaudhri | G06F 3/013 |
| 9,324,006 B2 | 4/2016 | Vanhoucke et al. | |
| 9,401,144 B1* | 7/2016 | Garber | G10L 15/22 |
| 9,529,428 B1 | 12/2016 | Bhattacharya et al. | |
| 9,535,497 B2 | 1/2017 | Rose et al. | |
| 9,557,811 B1 | 1/2017 | Bozarth | |
| 9,632,661 B2* | 4/2017 | Waldman | G06F 3/04817 |
| 9,753,533 B2* | 9/2017 | Bonnat | G06F 3/0346 |
| 10,134,084 B1* | 11/2018 | Gabriele | G06F 3/017 |
| 10,139,904 B2* | 11/2018 | Dow | G06F 3/0488 |
| 10,360,254 B1* | 7/2019 | Knas | G06F 3/013 |
| 10,474,342 B2* | 11/2019 | Gup | G06F 3/011 |
| 10,552,183 B2* | 2/2020 | Gordon | G06F 3/015 |
| 10,725,734 B2* | 7/2020 | Doi | G06F 3/167 |
| 2002/0133521 A1* | 9/2002 | Campbell | G06F 40/10 715/256 |
| 2003/0038754 A1* | 2/2003 | Goldstein | G06F 3/013 345/7 |
| 2004/0250220 A1* | 12/2004 | Kalenius | G06F 1/1626 715/864 |
| 2005/0047629 A1* | 3/2005 | Farrell | G06F 3/0481 382/117 |
| 2005/0246619 A1* | 11/2005 | Krause | G06F 3/012 715/277 |
| 2006/0281543 A1* | 12/2006 | Sutton | A61B 5/486 463/29 |
| 2007/0209017 A1* | 9/2007 | Gupta | G06F 3/0485 715/781 |
| 2007/0282912 A1* | 12/2007 | Reiner | G16H 10/20 |
| 2008/0141126 A1* | 6/2008 | Johnson | G06F 40/106 715/273 |
| 2009/0244003 A1* | 10/2009 | Bonnat | G06F 3/011 345/157 |
| 2010/0070912 A1* | 3/2010 | Zannan | G06F 3/0481 715/784 |
| 2010/0125807 A1 | 5/2010 | Easterday et al. | |
| 2010/0194754 A1* | 8/2010 | Alsbury | G06T 11/206 345/440 |
| 2011/0004327 A1* | 1/2011 | Bonnat | G06F 3/0346 700/83 |
| 2012/0005623 A1* | 1/2012 | Ishak | G06F 3/0485 715/786 |
| 2012/0054672 A1* | 3/2012 | McDowell | G09B 17/003 715/784 |
| 2012/0192121 A1* | 7/2012 | Bonnat | G06F 3/0488 715/863 |
| 2012/0256967 A1* | 10/2012 | Baldwin | G06F 3/0485 345/684 |
| 2013/0021373 A1* | 1/2013 | Vaught | G06F 3/013 345/633 |
| 2013/0027302 A1* | 1/2013 | Iwaizumi | G06F 1/1686 345/158 |
| 2013/0036357 A1* | 2/2013 | Hendrickson | G06F 3/0485 715/728 |
| 2013/0114043 A1* | 5/2013 | Balan | A61B 3/113 351/210 |
| 2013/0265231 A1* | 10/2013 | Cleveland | G06F 19/00 345/158 |
| 2013/0300654 A1* | 11/2013 | Seki | G06F 3/013 345/156 |
| 2013/0321473 A1* | 12/2013 | Tsuda | G09G 5/14 345/684 |
| 2014/0078049 A1* | 3/2014 | Parshionikar | G06K 9/00671 345/156 |
| 2014/0142397 A1* | 5/2014 | Bedrosian | G06K 9/00302 600/301 |
| 2014/0191948 A1* | 7/2014 | Kim | G06F 3/0483 345/156 |
| 2014/0223462 A1* | 8/2014 | Aimone | H04N 21/42201 725/10 |
| 2014/0240363 A1* | 8/2014 | Hong | G09G 5/34 345/684 |
| 2014/0247210 A1* | 9/2014 | Henderek | G06F 3/012 345/156 |
| 2014/0268054 A1* | 9/2014 | Olsson | G06K 9/00604 351/209 |
| 2014/0347265 A1 | 11/2014 | Aimone et al. | |
| 2015/0022438 A1* | 1/2015 | Hong | G06F 3/0346 345/156 |
| 2015/0109200 A1* | 4/2015 | Lee | G06F 3/012 345/156 |
| 2015/0128075 A1* | 5/2015 | Kempinski | G06F 3/013 715/765 |
| 2015/0169832 A1 | 6/2015 | Davis et al. | |
| 2015/0206011 A1 | 7/2015 | Jerauld | |
| 2015/0206321 A1* | 7/2015 | Scavezze | G06F 3/0485 345/633 |
| 2015/0331240 A1* | 11/2015 | Poulos | G06T 19/006 345/8 |
| 2015/0338914 A1* | 11/2015 | Andrysco | G06F 3/013 345/173 |
| 2015/0338917 A1* | 11/2015 | Steiner | H04M 1/7253 345/156 |
| 2015/0350201 A1* | 12/2015 | Cornell | H04L 63/0861 726/7 |
| 2016/0057374 A1* | 2/2016 | Kim | H04N 21/4223 348/734 |
| 2016/0062452 A1* | 3/2016 | Kim | G06F 3/011 345/661 |
| 2016/0078848 A1* | 3/2016 | Tanaka | G06F 3/013 345/684 |
| 2016/0080720 A1* | 3/2016 | Fullam | G02B 27/0093 345/156 |
| 2016/0170580 A1* | 6/2016 | Cho | G06F 3/167 715/716 |
| 2016/0299354 A1 | 10/2016 | Shtukater | |
| 2016/0349936 A1* | 12/2016 | Cho | G06F 3/04886 |
| 2016/0349970 A1* | 12/2016 | Everitt | G06T 3/40 |
| 2016/0358003 A1* | 12/2016 | Shen | G06K 9/0002 |
| 2017/0071537 A1* | 3/2017 | Jain | A61B 5/7203 |
| 2017/0083086 A1* | 3/2017 | Mazur | G06F 3/0484 |
| 2017/0090561 A1* | 3/2017 | Dow | G06F 21/32 |
| 2017/0102917 A1* | 4/2017 | Park | G02B 27/0179 |
| 2017/0112446 A1* | 4/2017 | Dagum | A61B 5/0476 |
| 2017/0168703 A1* | 6/2017 | Feris | G06F 3/011 |
| 2017/0212583 A1* | 7/2017 | Krasadakis | G06F 3/0485 |
| 2017/0265798 A1* | 9/2017 | Sales | A61B 7/04 |
| 2017/0351393 A1* | 12/2017 | Ott | G06F 3/04842 |

(56) References Cited

U.S. PATENT DOCUMENTS

2018/0181370 A1\* 6/2018 Parkinson ............. G06F 1/1686
2018/0292895 A1\* 10/2018 Schluessler ............ G06F 3/011
2020/0034031 A1\* 1/2020 Feris ...................... G06F 3/013
2020/0112835 A1\* 4/2020 Li ........................ G06Q 30/0261

\* cited by examiner

UTILIZING BIOMETRIC FEEDBACK TO ALLOW USERS TO SCROLL CONTENT INTO A VIEWABLE DISPLAY AREA

BACKGROUND

1. Technical Field

Present invention embodiments relate to utilizing biometric feedback to control a display of a device, and more specifically, to controlling the display and scrolling of content into a viewable display area on a display of the device.

2. Discussion of the Related Art

Motor impairment is the partial or total loss of function of a body part such as movement of a limb, head movement, or eye movement. The impairment may result in muscle weakness, poor stamina, lack of muscle control, or partial or total paralysis, which can result from a variety of neurological conditions such as cerebral palsy, Parkinson's disease, stroke, amyotrophic lateral sclerosis, or multiple sclerosis.

An extreme form of motor impairment is "locked-in syndrome", in which the body and most of the facial muscles are paralyzed. In less extreme cases, this impairment leaves the person with limited movement of the head, eyes, arms, and/or hands, while the person largely retains cognitive function. In more extreme cases, the person may lose all or almost all of their ability to move altogether.

Typically, users read content on electronic devices by moving their head and/or eyes from left to right, as the user needs to move his or her head or eyes to align with content. The movement of the head and eyes determines the reading speed of the user. When the user reaches the end of a page, user input from a keyboard or mouse is needed to scroll to unread content.

While effective for individuals who are not affected by neurological diseases, this method of scrolling is not a workable solution to those with impaired motor control. Impaired users frequently are not able to move their head or eyes to view content in all locations of the display, nor do they have the ability to move the display with their own hands to position content into a viewable display area. The impaired user can see a specific fixed area of the display in a stationary position.

Thus, it is difficult for a user with impaired motor control to read the content or view other contextually relevant objects on a device with a display.

SUMMARY

According to embodiments of the present invention, visual content is displayed on an electronic device to a user. For the user, a viewable display area on a display of the device is determined, and biometric data is obtained from the user. The biometric data is used to determine which state of a plurality of states that the user is in. Each state of the user is mapped to one or more control functions, and a control function is selected based on the state of the user. The selected control function is used to control scrolling of visual content through the viewable display area on the display of the electronic device.

Accordingly, methods, systems and computer readable media for displaying visual content on the electronic device to an impaired user are provided herein. Content may include text, images, spreadsheets, social media feed or any other form of data that may be subject to scrolling on an electronic device.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components. Through the more detailed description of some embodiments of the present disclosure in the accompanying drawings, the above and other features and advantages of the present disclosure will become more apparent.

DETAILED DESCRIPTION

Figure 1:
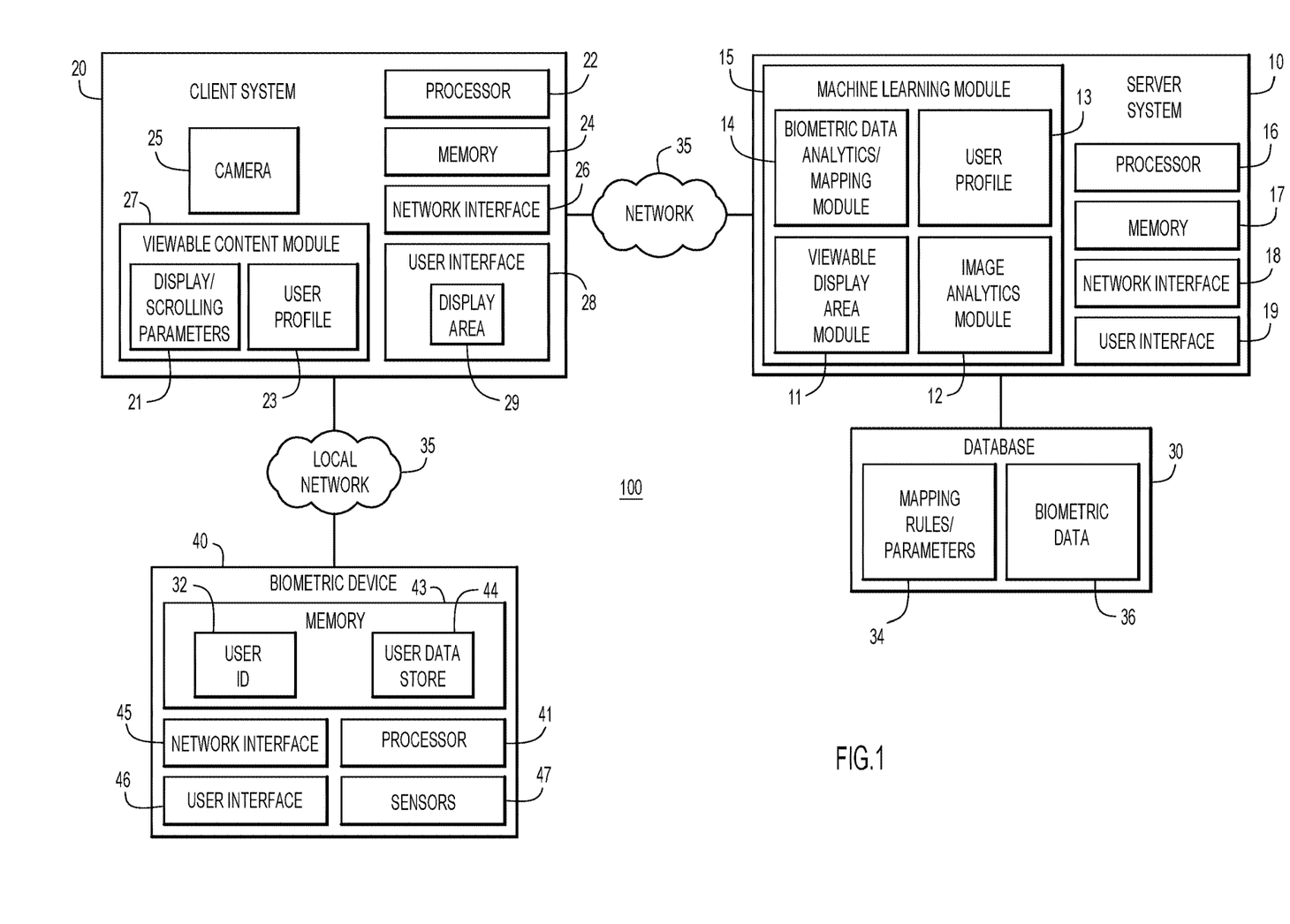
FIG. 1 is a block diagram of an example computing environment in accordance with embodiments of the present disclosure.

With reference now to FIG. 1 and in accordance with embodiments of the present disclosure, a block diagram of an example computing environment for a biometric content displaying system 100 is provided.

Specifically, the environment includes one or more server systems 10, and one or more client or end-user systems 20. Server systems 10 and client systems 20 may be remote from each other and may communicate over a network 35. The network may be implemented by any number of any suitable communications media (e.g., wide area network (WAN), local area network (LAN), Internet, Intranet, etc.). Alternatively, server systems 10 and client systems 10 may be local to each other, and may communicate via any appropriate local communication medium (e.g., local area network (LAN), hardwire, wireless link, Intranet, etc.).

Client systems 20 enable impaired users to view content (e.g., text documents, spreadsheets, images, etc.) by scrolling visual content through a viewable display area. Client systems 20 may be implemented by any conventional or other computer systems preferably equipped with a display or monitor, a base (e.g., including at least one processor 22, one or more memories 24 and/or internal or external network interfaces or communications devices 26 (e.g., modem, network cards, etc.)), optional input devices (e.g., a keyboard, mouse or other input device), and any commercially available and custom software (e.g., server/communications software, viewable content module 27, browser/interface software, etc.). User interface 28 includes a display area 29 for the display of visual content.

Viewable content module 27 contains information for controlling the display of viewable content for a particular user. For example, display and scrolling parameters 21 determine the speed and orientation of content that is scrolled through a viewable display area, which may be a portion of the display area 29. Client system 20 also includes a camera 25, for obtaining images of the impaired user. These images may be sent to server system 10, wherein the images are analyzed to determine the viewable display area for a particular user.

The client system 20 may include camera 25, which is used to take images of the user. The images can be processed by the machine learning module 15 of server system 10, and in particular viewable display area module 11, to determine the user's facial tilt (e.g., angle of the user's face with respect to the display), eye focus, and viewing angle with respect to the display. These parameters can be used to determine location area(s) on the display that the user can view, to identify the primary focus area on the display screen (the viewable display area), and to which the viewable content will be directed and automatically scrolled, allowing the user to read the content without moving their head or eyes. In some embodiments, once the viewable display area is determined, the user is presented with a request to confirm calibration of the system, e.g., confirmation may be provided by biometric data from wearable devices.

Prior to operation, the client device comprising the display area 29 may be configured with a user profile 23, to interact with wearable biometric devices 40, to communicate with the server system 10, and may include information to identify the user corresponding to the user profile.

The server systems 10 include a machine learning module/cognitive system 15 to provide visual content to an impaired user. Server systems 10 may be implemented by any conventional or other computer systems preferably equipped with a display or monitor, a base (e.g., including at least one processor 16, one or more memories 17 and/or internal or external network interfaces or communications devices 18 (e.g., modem, network cards, etc.)), user interface 19 which may include optional input devices (e.g., a keyboard, mouse or other input device), and any commercially available and custom software (e.g., server/communications software, machine learning module 15, etc.). Machine learning module 15 may comprise multiple modules including viewable display area module 11, image analytics module 12, user profile 13, and biometrics data analytics/mapping module 14, which are involved in generating, controlling the display of, and providing viewable content to the user. Viewable display area module 11 receives images from camera 25 of client system 20, determines a user's orientation with respect to the display screen (e.g., eye/head angle relative to screen, distance from screen, etc.) and calculates a viewable display area for an impaired user based upon this information. Viewable display area module 11 may also provide default viewable display area parameters at initialization, setting a default size for a viewable display area until the area can be customized to a particular user. Viewable display area module 11 may also increase or decrease the size of the viewable display area in response to obtained biometric data or other data indicating that a patient's range of vision has changed.

Image analytics module 12 may divide contextual objects (e.g., photos) into multiple sections, according to the embodiments provided herein. Image analytics may be performed to extract objects from an image, identify objects or people within the image, as well as perform contextual analysis to determine relevance of objects or people from other data sources (e.g., social media, metadata, etc.).

User profile 13 comprises information to identify the user, in order to select and apply corresponding stored customized scrolling parameters / mapping rules 34 for a particular user. Stored parameters may include a speed of scrolling, a direction of scrolling, etc. Stored mapping rules may map biometric data obtained from a user to a state of a user. States of a user are mapped to corresponding control functions for controlling the passage of visual content through the viewable display area. A user may be identified, based on identification of a wearable device (biometric device 40) specific to that user, based on facial image recognition performed by image analytics module 12 from images provided by camera 25, or from voice recognition, if applicable.

The machine learning system 15 may be used to perform facial recognition or voice recognition or device recognition to identify users registered with the system. In general, each impaired user will have their own user profile at the client and server system, and the client system 20 may be configured to be paired with one or more wearable devices.

Biometrics data analytics/mapping module 14 may map received biometric data to a user state, as well as a user state to one or more control functions (e.g., to increase or decrease a rate of display (scrolling), to scroll right, left, up, down, to pause for a specified interval, provide confirmation, etc.). In some aspects, once scrolling initiates, biometric data analytics/mapping module 14 may continuously map received biometric data to a user state, e.g., in real-time or near real time, and may continuously select control functions for controlling the display of visual content. Motor impaired users have different conditions and severity, thus, the biometric data analytics/mapping module 14 may be utilized to map a range of conditions and functionality to a particular user, e.g., range of motion of head (e.g., none, up, down, left, right); range of motion of eye movement (none, up, down, left, right), etc. The biometric data analytics/mapping module 14 may also utilize natural language processing techniques to perform the various analytics and mapping functions provided herein.

Biometric data can be mapped to the following (navigation) control functions using module 14, wherein the functions include but are not limited to: (1) controlling the speed at which visual content is scrolled; (2) pausing scrolling; or (3) controlling a direction of scrolling (e.g., scrolling left (to redisplay content), scrolling right (to display unread content), scrolling up (to review content), scrolling down (to display unread content)). Each of these control functions can be adjusted based on biometric data fed back into the display device. The control functions may be associated with one or more parameters, for example, a speed of scrolling, a length of pausing, a direction or angle of scrolling, etc. In some embodiments, eye contact with the viewable display area may be monitored, and a user staring at an edge of the viewable display area may be interpreted as indicating a direction of scrolling (e.g., starting at an upper edge may indicate scrolling up and at a lower edge as scrolling down).

A database system 30 may store various information for the analysis (e.g., mapping rules 34 to control mapping of biometric data to a state of a particular user and of a state to a control function, and biometric data 36 that contains stored biometric data for a particular user). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the display of visual content.

Alternatively, one or more client systems 20 may provide content scrolling through a viewable display area, when operating as a stand-alone unit. In a stand-alone mode of operation, the client system stores or has access to the data (e.g., biometric data 36, user profile 23, mapping rules 34, etc.), and includes machine learning module 15 to determine a viewable display area, perform image analysis, and provide display and scrolling parameters 21 to viewable content module 27 based on a state of a user. The graphical user (e.g., GUI, etc.) or other interface (e.g., command line prompts, menu screens, etc.) may solicit information from a corresponding user pertaining to the display of visual content.

Modules (viewable content module 27 and machine learning module/cognitive machine 15) may include one or more modules or units to perform the various functions of present invention embodiments described herein. The various modules (e.g., viewable content module 27 and machine learning module 15) may be implemented by any combination of any quantity of software and/or hardware modules or units, and may reside within memory 17, 24 for execution by processor 16, 22 of the server and client systems respectfully.

The machine learning module 15, which is a cognitive system, may correlate or map one or more types of biometric data to a user state, e.g., a state corresponding to an emotion (e.g., non-stressed, stressed, lack of interest, etc.). For example, a user may be become stressed or frustrated that content being scrolled through the viewable display area is too slow. Biometric data or other data may be received (e.g., a change of voice tone indicating boredom, a facial expression, a change in respiration such as sighing, loss of eye contact indicating distraction, etc.), and the biometric data mapping module 14 may determine a state (e.g., stressed from slow content scrolling) of the user from the biometric data. This state may be mapped to control functions with corresponding parameters configured to increase the scrolling speed.

As another example, biometric data or other data may indicate frustration from a rate of scrolling that is too fast (e.g., an elevated heart rate, a change in voice tone signaling anxiety, a facial expression, rapid eye movement, etc.). In this case, the machine learning system 15 may determine a state (e.g., stressed from fast content scrolling) of the user, and may select the corresponding control function configured to decrease the scrolling rate.

In aspects in which it is not clear whether an increase or decrease in scrolling speed of visual content is needed, the machine learning system 15 may select a first control function, and if the state of the user does not change or becomes worse (as compared to a baseline state of little or no stress), the machine learning system 15 may then select a second (opposite) control function. If the user's physiological response returns to the baseline, then no further adjustments to the scrolling speed will be made. Thus, the machine learning system may select different control functions until determining that user stress as evidenced by the biometric data has been reduced. In this case, the machine learning system may identify biometric data that corresponds to user stress.

The machine learning system 15 may also contain a user profile 13, which stores parameters specific to the user, to control the flow of content through the viewable display area. The user profile 13 may also associate a particular user with one or more particular wearable biometric devices 40. The parameters for controlling the flow of content through the viewable display area may also be sent to client system 20, for local storage as display scrolling parameters 21.

Client system 20 is generally local to biometric device 40. In some embodiments, local network 35 may be a WiFi® network, connecting the biometric device to the client system.

Biometric device 40 may be implemented by any conventional or other device preferably equipped with a display or user interface 46, a base (e.g., including at least one processor 41, one or more memories 43 and/or internal network interfaces or communications devices 45 (e.g., antennae for WiFi®, etc.)), optional input devices (e.g., buttons, touch screen, etc.), any commercially available and custom software (e.g., client/communications software, operating system software, etc.), and sensors 47. Sensors 47 in the biometric device provide the ability to capture biometric data including but not limited to pulse, blood pressure, heart rate, brain wave signals, EKG signals, bodily temperature, respiration rate, perspiration rate, etc.

Biometric device 40 transmits the biometric data, which may be temporally stored as a function of time in user data store 44 prior to transmission, to client system 20. The client system 20 then transmits the biometric data to server system 10 for analysis. In some embodiments, each biometric device has its own user ID 32 to identify the corresponding wearable device 40 to client system 20. Client system 20 may correlate biometric devices for a particular user, in the case where a user is wearing multiple biometric devices 40. In some embodiments, client system 20 may interface directly with biometric device 40 to configure biometric device 40 for particular types of data collection at specific frequencies of collection.

Examples of biometric devices include a smart watch, e.g., which has a sensor to measure the current user heart rate of an impaired user, which can be streamed in real-time as a measure of an emotional or physiological state, which is mapped to a state to control scrolling aspects of visual content.

Other examples include an electronic tattoo, which has sensors to detect a physical movement such as a frown or other facial movement indicating a user state. Electronic tattoos may be located on a user's face (e.g., temple, cheek, etc.) or other appropriate location. Data can be streamed from the electronic tattoo to a mobile device or client device, for evaluation or mapping, or in turn may be transmitted to the machine learning system for analysis.

Other examples include smart contacts, which have a camera (e.g., inward/outward), sensors, antenna, and the ability to stream real-time data for analysis. Smart contacts can measure pupil dilation, which may be used as an indicator of emotion (e.g., attention, stress, focus level, etc.) to determine mapping of control functions.

It will be appreciated that many different types of computing environments are suitable for present invention embodiments. In some cases, server system 10 will perform the operations associated with determining a viewable display area, with analyzing and mapping biometric data, with image analysis, and so forth. In other cases, client system 20 will perform the operations associated with determining a viewable display area, with analyzing and mapping biometric data, with image analysis and so forth. In still other cases, these operations may be distributed between server system 10 and client system 20. In general, the biometric device 40 will communicate locally with the client system 20, e.g., using a WiFi® connection. However, in other embodiments, biometric device 40 may communicate directly with server system 40.

Figure 2:
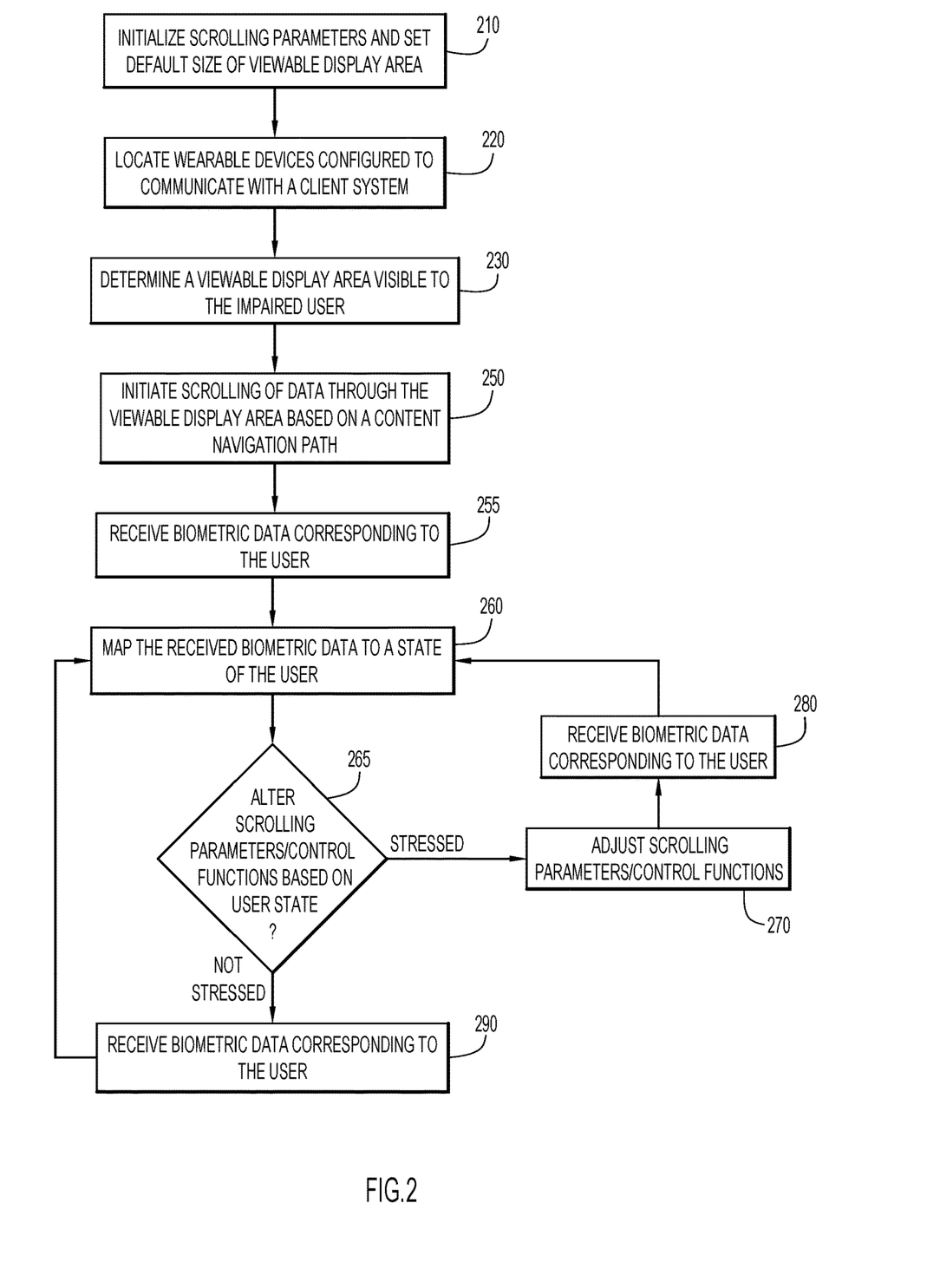
FIG. 2 is a flowchart of an example computer-implemented method of utilizing biometric feedback to control scrolling of content according to an embodiment of the present disclosure.

Referring to FIG. 2, the following operations may be performed to move content via horizontal or vertical scrolling into the viewable display area of the display area 29. At operation 210, a default viewable display area of the display device is selected and scrolling is initialized with default parameters. At operation 220, the cognitive component locates wearable devices within range (e.g., a WiFi® or other local network) that are configured to communicate with the user client system 20. Additionally, the identity of the user may be determined from the wearable device 40 or from facial recognition analysis performed on images generated by camera 25. At operation 230, the viewable display area of the display that is visible to the (impaired) user is determined based on image analysis (e.g., eye/head angle relative to screen, distance from screen, etc.). Here, the machine learning system determines the position of the user, namely, the user's eye focus and viewing angle relative to the display (e.g., using images from the camera) to determine the viewable display area, which may be larger, smaller or the same as the default viewable display area.

The user may optionally be prompted to confirm the viewable display area is visible, e.g., through verbal commands, or with physiological feedback provided from the wearable biometric device. Once the viewable display area has been confirmed, viewable content may be moved into the viewable display area, and scrolled in a manner to allow the impaired user to read the content.

At operation 250, scrolling begins using a content navigation path. The content navigation path determines how information is scrolled through the viewable display area. At operation 255, biometric data is received and at operation 260, the collected data is analyzed, mapping the biometric data to a state of the user. At operation 265, a determination is made as to whether the user is in a stressed or non-stressed state. If the user is not in a stressed state, biometric data continues to be received at operation 290, and the state of the user continues to be monitored at operations 260 and 265, without changes being made to the scrolling control functions or associated parameters. If the user is in a stressed state, changes are made to the scrolling parameters and/or scrolling control functions at operation 270, and biometric data continues to be received at operation 280. The state of the user continues to be monitored at operations 260 and 265.

Thus, biometric data may be used to adjust scrolling parameters (e.g., the scrolling speed, direction, etc.) to tailor or customize display of content through the viewable display area to a particular user's condition and function. The user can provide different physiological responses detected by sensors in the wearable device or by verbal commands to implement specific scrolling actions. In other aspects, such feedback may be provided via a care provider.

Text may be scrolled horizontally or vertically through the viewable display area, and characteristics of scrolling may continue to be adjusted based on biometric data from the user. Data from wearable devices such as smartwatch devices or electronic tattoos, may provide real-time or near real-time biometric data which is mapped to a state of the user. Feedback of biometric data is used to continually adjust navigation of visual content.

Examples of physiological responses or other factors which reflect a state of the user include, but are not limited to, any measureable physiological response associated with stress or lack of stress such as increased or decreased heartrate, facial expressions, increased or decreased respiration, increased or decreased perspiration, focusing of eyes, rate of eye blinking, voice intonations, and non-verbal sounds. Each of these responses, alone or in combination, can be correlated with a state of the user, e.g., a state of stress or lack of stress, interest or lack of interest, etc. If the data indicates a state of stress, the scrolling parameters and control functions of the device can be adjusted (e.g., sped up or slowed down) to suit the user. If the responses indicate a state of non-stress, the scrolling parameters and control functions will remain the same or about the same. Various physiological data can be mapped to two or more states, reflecting stress or lack thereof, to control the scrolling of visual content through the viewable display area of the device.

In other embodiments, content may be moved into the viewable display area based on a content navigation path according to a default configuration, e.g., a default configuration which positions the visual content from the beginning of the text-based object (e.g., an upper rightmost section, beginning of a page, beginning of a chapter).

In additional embodiments, the user is impaired but is able speak at a sufficient level to issue commands to the cognitive system. For example, speech may be used as a direct navigation method to move viewable content into the viewable display area. In some cases, contextual analysis using Natural Language Processing (NLP) may be performed on the user's speech to determine content the user seeks to view. For example, an impaired user may use voice as input to say "view ABC chapter, heading" with reference to a document. The system would identify the chapter with the appropriate heading, and move this text into the viewable display area of display.

In still other embodiments, the content navigation path may be based on metadata or other information. In still other embodiments, the content navigation path is based on relevance or ranking of results for display into the viewable display area. In other embodiments, the content navigation path may be based on a chronological order.

Figure 3A:
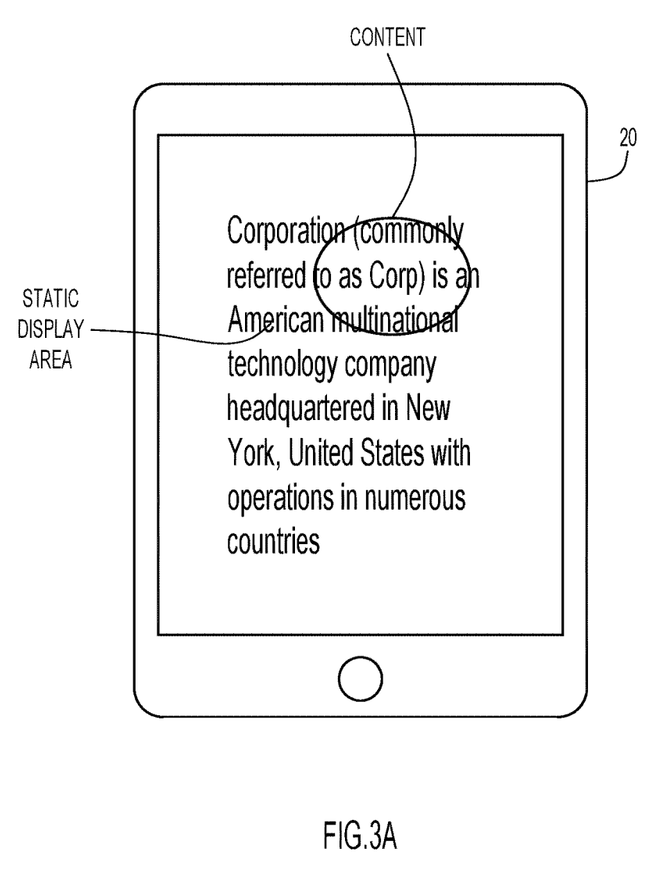
FIGS. 3A-3B are example illustrations showing a viewable display area of text for an unimpaired user (FIG. 3A) and an impaired user (FIG. 3B) in accordance with embodiments of the present disclosure.
Figure 3B:
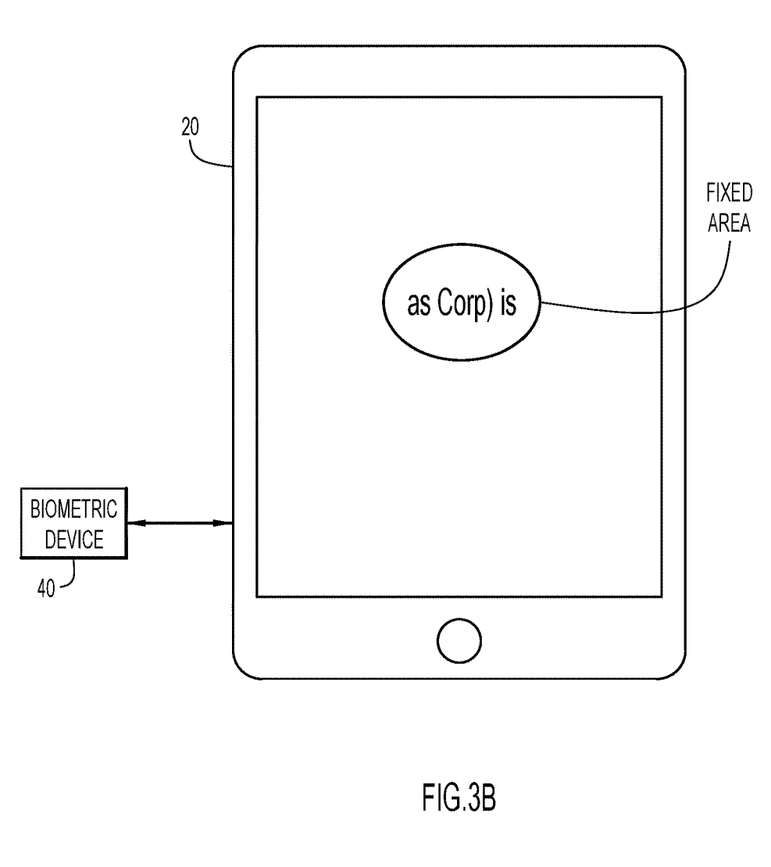

FIG. 3A is an illustration showing the entire display screen of a device, which a person without a motor impairment is able to read. FIG. 3B shows a fixed area, or viewable display area, visible to a motor impaired user. As the user is unable to move or may have limited movement of their head or eyes, the impaired user is not able to view the entire display, and is limited to a particular fixed area on the display screen.

Figure 4A:
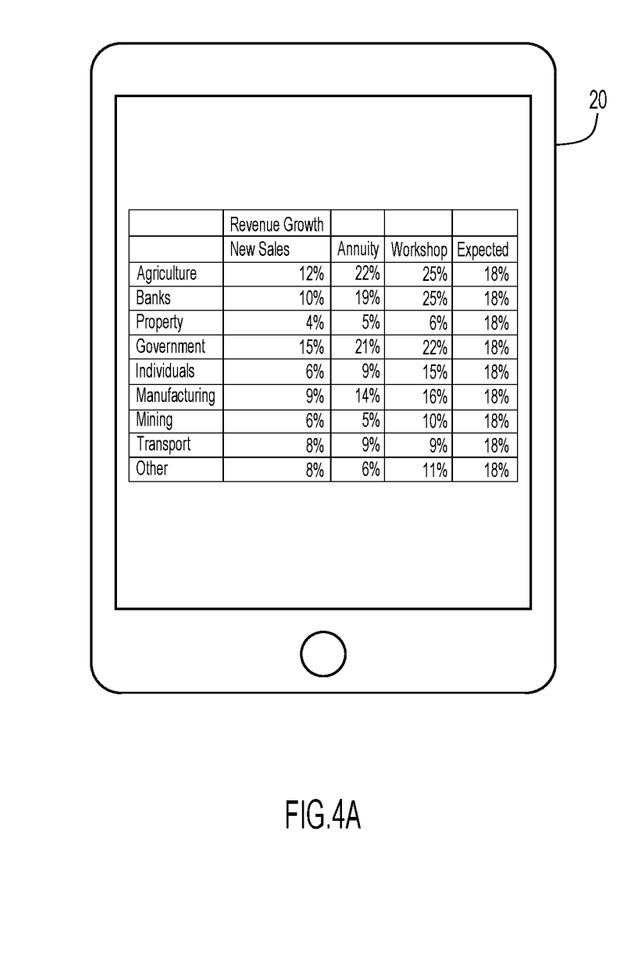
FIGS. 4A-4B are example illustrations showing a viewable display area of a spreadsheet for an unimpaired user (FIG. 4A) and an impaired user (FIG. 4B) in accordance with embodiments of the present disclosure.
Figure 4B:
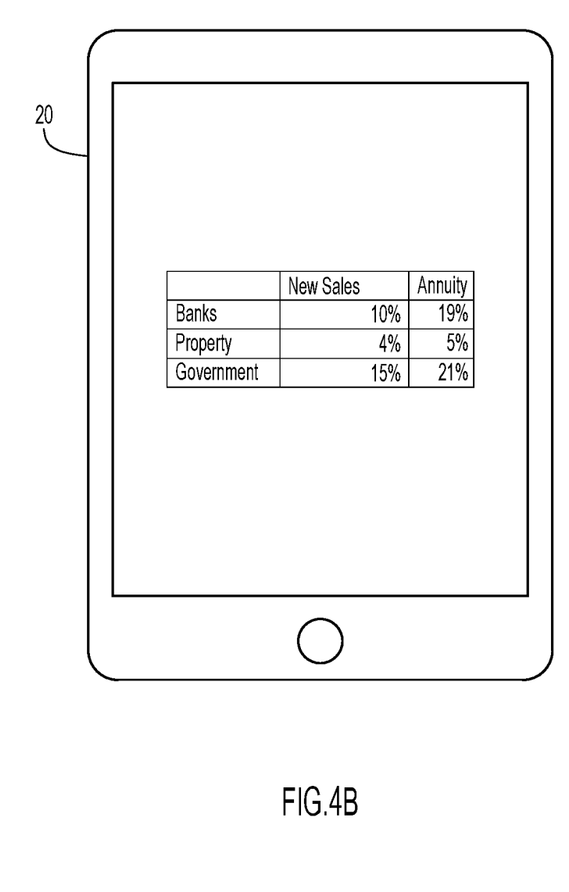

FIGS. 4A-4B show another example embodiment, in which spreadsheet content (e.g., rows and/or columns) are scrolled into the viewable display area of the display. FIG. 4A shows displaying an entire spreadsheet on the display of a device. However, an impaired user is not able to view the entire image, and therefore, machine learning system 15 may divide the spreadsheet into small segments of rows and columns for display in a viewable display area to the impaired user as shown in FIG. 4B. In other embodiments, content may be moved into the viewable display area based on a content navigation path according to a default configuration, e.g., a default configuration which positions the visual content from the beginning of the spreadsheet-based object (e.g., an upper rightmost section, etc.).

In additional embodiments, the user is impaired but is able speak at a sufficient level to issue commands to the cognitive system. For example, speech may be used as a direct navigation method to move viewable content into the viewable display area. In some cases, contextual analysis using Natural Language Processing (NLP) may be performed on the user's speech to determine content the user seeks to view. For example, an impaired user may use voice as input to say "column, new sales" to view a particular column of a spreadsheet). The software would identify the column with the appropriate heading, and would move this data into the viewable display area of display.

In some embodiments, the titles of the rows and/or columns may remain fixed, so that only changes in data are visualized while scrolling.

Similar to scrolling text, the spreadsheet content is scrolled horizontally or vertically through the viewable display area depending on real-time or near real-time biometric data from the user. Biometric devices may be provided by wearable devices, e.g., smartwatches, electronic tattoos, etc.

Figure 5A:
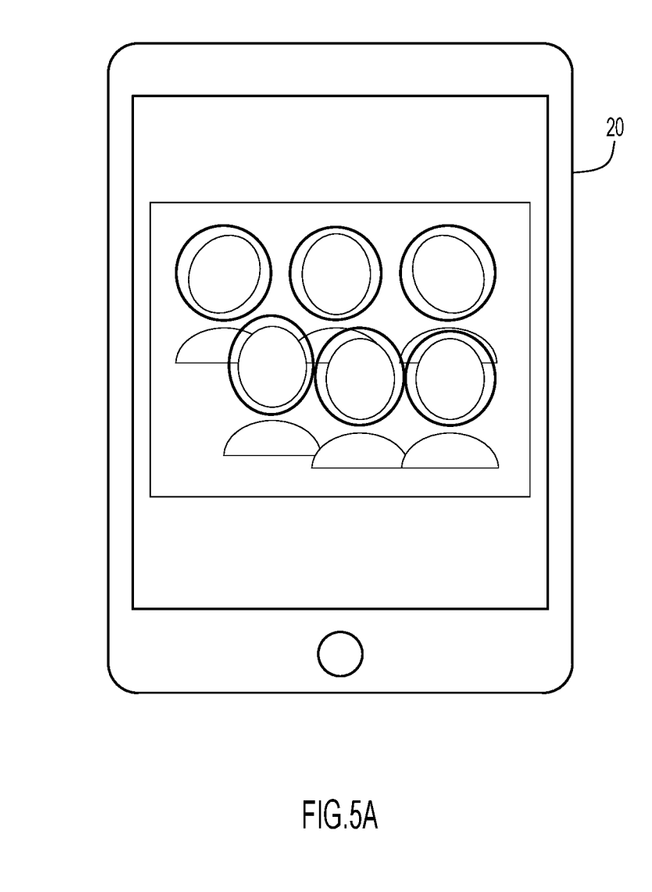
FIGS. 5A-5B are example illustrations showing a viewable display area of a contextual object for an unimpaired user (FIG. 5A) and an impaired user (FIG. 5B) in accordance with embodiments of the present disclosure.
Figure 5B:
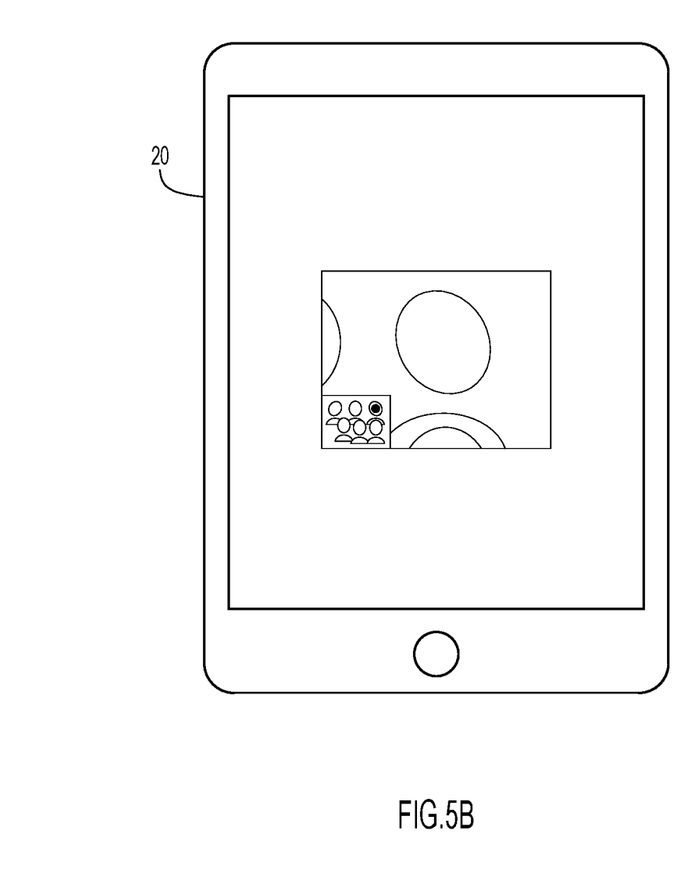

FIGS. 5A-5B show an embodiment of controlling the display (e.g., scrolling) of contextual objects (e.g., a photo or image, etc.) for a motor impaired user. FIG. 5A shows displaying an entire image on the display of a device. However, an impaired user is not able to view the entire image, and therefore, the machine learning system 15 may divide the contextual object (e.g., image or photo) into multiple sections comprising key objects for display in a viewable display area to the impaired user, as shown in FIG. 5B. In some embodiments, analysis of the contextual object may be used to identify key objects of the image, which may include but are not limited to individuals, and may be utilized to position sections within a photo or image into the viewable display area.

For images of individuals, facial recognition technology may be used to identify the presence of each individual, and the image may be divided into sections that are displayed to the user in a sequential manner. In some embodiments, each section may comprise a single individual. In other embodiments, each section may comprise multiple individuals.

The currently displayed section may change to a different displayed section of the contextual object based on instructions, including but not limited to, changing sections at a preset time (e.g., a timed interval), verbal instructions to change to a different section, or changing sections based on biometric data obtained from the user (e.g., to determine a scrolling speed or direction).

A display order or content navigation path may be established to determine an order in which sections are presented to the user. In some embodiments, the content navigation path may be based on adjacent sections. In other embodiments, the content navigation path may be random.

In other embodiments, content may be moved into the viewable display area according to a default configuration, e.g., a default configuration which positions the visual content from the beginning of the contextual object (e.g., an upper rightmost section).

In still other embodiments, the content navigation path may be based on the relevance of the key object, as determined by metadata or other information. For example, a photograph or other image may have a plurality of key objects of contextual relevance. In a photo with multiple people, the relevance of a particular person is determined by the respective user. In a photo having multiple family members, each person in the photo is of a different relevance to a user in a set of users. By coupling the identity of the user to the contextual object, relevance for a particular user can be determined.

In still other embodiments, the content navigation path may be based on the prominence of the key object in the section, e.g., such that in an image with key objects of varying sizes, the key objects will be presented in a display order of decreasing size of the key object.

In additional embodiments, the user is impaired but is able speak at a sufficient level to issue commands to the cognitive/machine learning system 15. For example, speech may be used as a direct navigation method to move sections into the viewable display area. In some cases, contextual analysis using Natural Language Processing (NLP) may be performed on the user's speech to determine which segment(s) the user seeks to view. A search can be performed to identify the segment(s) to display. For example, if a user issues a command to see an image of John, the segment containing metadata or other data identifying John can be selected for display.

Each of the key objects will be placed in the viewable display area, allowing the user to view the image completely by viewing a plurality of sections. In some aspects, a thumbnail of the image may be displayed in a corner of the device display to provide a reference to the user (e.g., a circle, arrow, dot, or other distinguishing mark) of the section that is being displayed relative to the contextual object (e.g., complete image).

Figure 6:
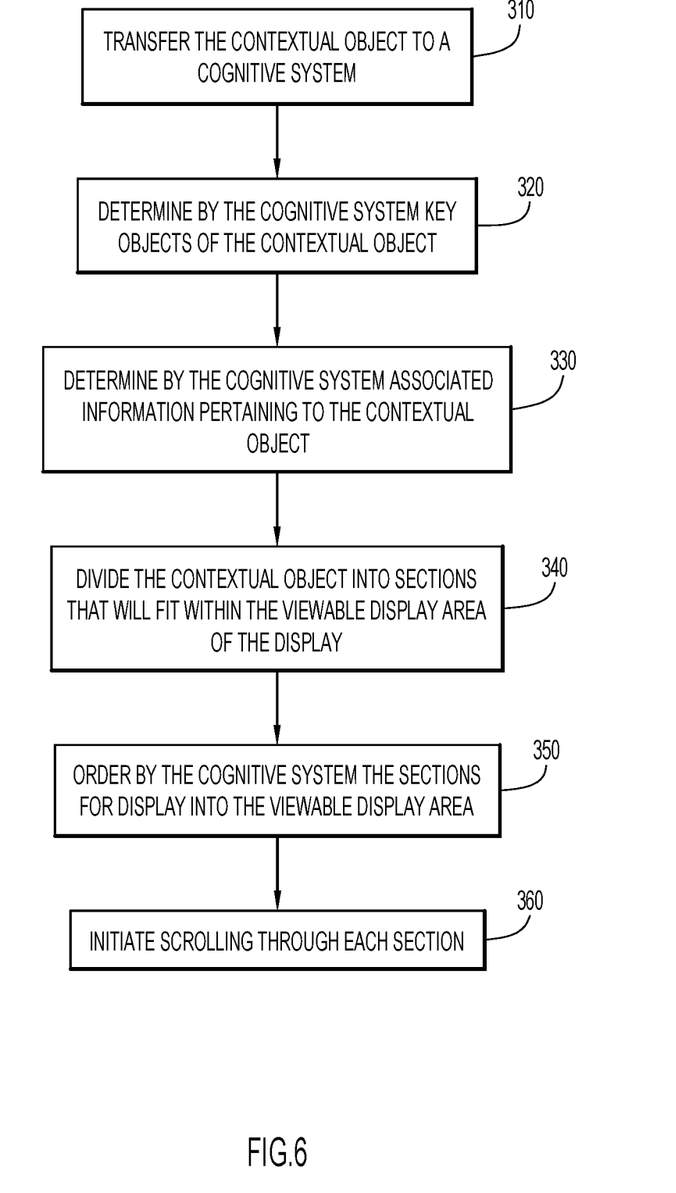
FIG. 6 is a flowchart of an example computer-implemented method of processing a contextual object into sections, in accordance with embodiments of the present disclosure.

Referring to FIG. 6, at operation 310, the contextual object (e.g., photo or image) is transferred to cognitive system/machine learning module 15. At operation 320, the cognitive system determines key objects (e.g., people, landscape features, etc.) of the contextual object. At operation 330, the cognitive system determines associated information pertaining to the contextual object (e.g., metadata, information associated with the photo from an online resource, etc.). For example, the cognitive/machine learning system may access online data sources such as social media pages associated with the photo to identify people or other information associated with the photo. At operation 340, the cognitive system divides the contextual object into a plurality of sections that will fit within the viewable display area of the display for the impaired user to visualize. At operation 350, the cognitive/machine learning system may order the sections for display into the viewable display area (e.g., random, based on adjacent images, relevance, prominence, etc.). For example, if it is John's birthday, then the section displaying John will be the most relevant section to display first. After John, other key objects which may be considered relevant are John's immediate family, followed by John's friends and colleagues. At operation 360, the cognitive system may scroll through each section, presenting each section within the viewable display area, in an order of relevance, as determined an operation 350. The user may control scrolling through sections of the contextually relevant object (e.g., left, right, up, down, speed of scrolling, etc.) using feedback of biometric data from the wearable device as provided herein (see, FIG. 2).

Figure 7:
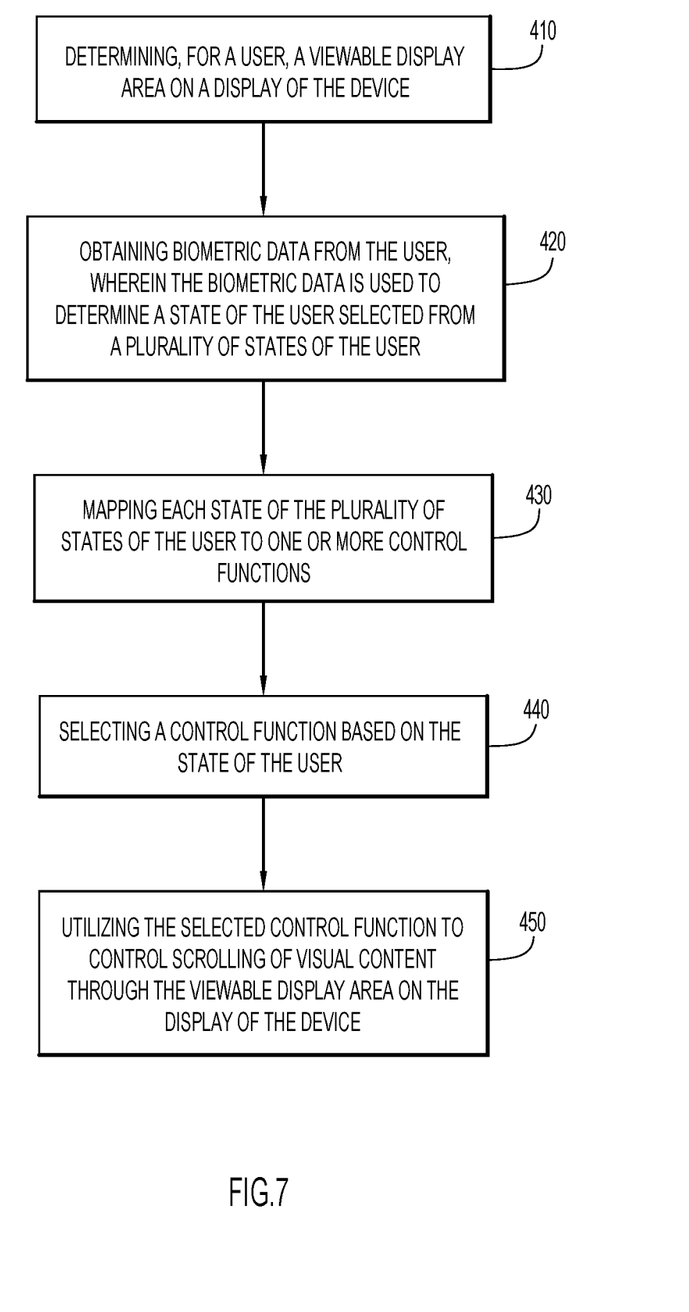
FIG. 7 is a flowchart of an example computer-implemented method of utilizing biometric feedback to control scrolling of content through a viewable display area in accordance with embodiments of the present disclosure.

FIG. 7 is an operational flow chart of the device at a high level. At operation 410, a viewable display area on a display of the device is determined for a user. At operation 420, biometric data is obtained from the user, wherein the biometric data is used to determine a state of the user selected from a plurality of states of the user. At operation 430, each state of the plurality of states is mapped to one or more control functions. At operation 440, a control function is selected based on a state (a current state) of the user. At operation 450, the selected control function is utilized to control scrolling of visual content through the viewable display area on the display of the electronic device.

In summary, various embodiments are provided herein for moving visual content into a viewable display area, to provide an impaired user with navigation control, e.g., using wearable biometric devices. By determining a specific area of a display that a user with an impairment can view (the viewable display area), the techniques provided herein may be used to control scrolling of visual content through the viewable display area to provide an impaired user with the ability to view visual content in its entirety.

In some aspects, the impaired user may suffer from any number of physical conditions or restriction which limit movement, including restricted head and/or eye movement due to disease or disability, motor impairment of limbs due to disease or disability, physical restraints preventing movement of arms or hands, physical supports such as a neck brace that limits movement, etc. Present invention embodiments may also be used for users lacking impairments. Biometric feedback from one or more wearable devices may be used to indicate a state of the user, and based upon the state of the user, the client device may be used to control scrolling operations (e.g., horizontal scrolling, vertical scrolling, pausing, speed of scrolling, size of font, etc.) of visual content through the viewable display area.

In an embodiment, the user is provided with the ability to move textual content via horizontal or vertical scrolling into a specific area of the viewable display area. In another embodiment, the user is provided with the ability to move spreadsheet content via scrolling for rows and columns into a specific area of the viewable display area. In yet another embodiment, the user is provided with the ability to identify key objects (e.g., such as people) in a contextual object (such as a photo). The photo may be divided into sections, and each section may be moved into the viewable display area to view key objects.

Advantages of present invention embodiments include providing impaired users (e.g., with a motor impairment) with the ability to move textual, spreadsheet, or contextual object visual content into the viewable display area, e.g., by scrolling text horizontally or vertically using navigation control functions based on a state of a user, wherein the state is determined by mapping biometric data obtained from wearable biometric devices to user states, and the user states to one or more predefined control functions. The biometric data may reflect an emotional, psychological, or physiological state of a user.

The system provided herein has advanced adaptive capabilities, using machine learning to map biometric data to user states, and the user states to control functions. As more information (biometric data) is provided to the system, the system improves its ability to determine how an impaired user intends to control the display of visual content. Thus, the techniques provided herein allow user customization of the system, as the system learns to adapt the display of visual content to the user, based on the user's particular physiological, emotional, and psychological inputs as provided by the biometric device and other devices.

Any of the present invention embodiments may be integrated with or may interface with artificial intelligence platforms, including but not limited to IBM Watson® (computer software).

It will be appreciated that the embodiments described above and illustrated in the drawings represent only a few of the many ways of implementing embodiments for displaying visual content in a viewable display area.

The environment of the present invention embodiments may include any number of computer or other processing systems (e.g., client or end-user systems, server systems, biometric devices, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, viewable content module 27, machine learning module 15, etc.). These systems may include any types of monitors and input devices (e.g., keyboard, mouse, voice recognition, etc.) to enter and/or view information.

It is to be understood that the software (e.g., viewable content module 27, machine learning module 15) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely from each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., viewable content module 27, machine learning module 15) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., biometric data 36, mapping rules and parameters 34, display and scrolling parameters 21, user profiles 23 and 13, etc.). The database system may be implemented by any number of any conventional or other databases, data stores or storage structures (e.g., files, databases, data structures, data or other repositories, etc.) to store information (e.g., biometric data 36, mapping rules and parameters 34, display scrolling parameters 21, user profiles 23 and 13). The database system may be included within or coupled to the server and/or client systems. The database systems and/or storage structures may be remote from or local to the computer or other processing systems, and may store any desired data (e.g., biometric data 36, mapping rules and parameters 34, display and scrolling parameters 21, user profiles 23 and 13).

The present invention embodiments may employ any number of any type of user interface (e.g., Graphical User Interface (GUI), command-line, prompt, etc.) for obtaining or providing information (e.g., biometric data 36, mapping rules and parameters 34, display and scrolling parameters 21, user profiles 23 and 13), where the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for any application involving display of information to any user, and preferably to an impaired user.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of providing visual content displayed on an electronic device to a motor-impaired user, the method comprising:
   determining, for the motor-impaired user, a viewable display area on a display of the electronic device, wherein the viewable display area is a fixed area corresponding to a stationary location on the display and wherein the viewable display area is smaller in size than the display;
   determining a baseline state of the motor-impaired user;
   analyzing the visual content to divide into multiple sections comprising key objects;
   dividing the visual content into the multiple sections;
   determining a content navigation path to scroll the multiple sections of the visual content based on a relevance or prominence of each key object of the key objects;
   automatically scrolling the visual content through the viewable display area according to the determined content navigation path;
   obtaining biometric data including motor-impaired user data from the motor-impaired user, wherein the biometric data is used by a cognitive control system having a processor to determine a state of the motor-impaired user selected from a plurality of states, the plurality of states corresponding to a stress or interest level of the motor-impaired user, and wherein the biometric data obtained from the motor-impaired user is selected from a group consisting of a heart rate, a tone of voice, and a rate of respiration;
   mapping, by the cognitive control system having the processor, each state of the plurality of states to one or more control functions;
   selecting a control function from the one or more control functions based on the determined state of the motor-impaired user; and
   adjusting, via the selected control function, the scrolling of the visual content outside the viewable display area through the viewable display area on the electronic device to return the determined state of the motor-impaired user to the baseline state, wherein additional biometric data is obtained and processed to determine that the determined state of the motor-impaired user has returned to the baseline state, and wherein the additional biometric data obtained from the motor-impaired user is selected from the group consisting of the heart rate, the tone of voice, and the rate of respiration.

2. The method of claim 1, wherein the viewable display area is determined by calculating a user distance and a viewing angle of the motor-impaired user relative to the display.

3. The method of claim 1, further comprising continuously modifying the one or more control functions to control the scrolling of the visual content based upon real-time or near real-time biometric data obtained from the motor-impaired user.

4. The method of claim 1, wherein the biometric data is obtained from one or more wearable biometric devices.

5. The method of claim 1, wherein the biometric data includes data corresponding to an emotional, psychological, or a physiological state of the motor-impaired user, and wherein a machine learning system maps the biometric data to the determined state of the motor-impaired user.

6. The method of claim 1, wherein the one or more control functions are scroll up, scroll left, scroll down, scroll right, provide confirmation, increase scrolling speed, decrease scrolling speed, or pause.

7. The method of claim 1, further comprising:
receiving a voice instruction from the motor-impaired user; and
moving the visual content into the viewable display area based on the voice instruction.

8. A system for providing visual content displayed on an electronic device to a motor-impaired user, the system comprising at least one processor configured to:
determine, for the motor-impaired user, a viewable display area on a display of the electronic device,
wherein the viewable display area is a fixed area corresponding to a stationary location on the display and wherein the viewable display area is smaller in size than the display;
determine a baseline state of the motor-impaired user;
analyze the visual content to divide into multiple sections comprising key objects;
divide the visual content into the multiple sections;
determine a content navigation path to scroll the multiple sections of the visual content based on a relevance or prominence of each key object of the key objects;
automatically scroll the visual content through the viewable display area according to the determined content navigation path;
obtain biometric data including motor-impaired user data from the motor-impaired user, wherein the biometric data is used by a cognitive control system via the at least one processor to determine a state of the motor-impaired user selected from a plurality of states, the plurality of states corresponding to a stress or interest level of the motor-impaired user, and wherein the biometric data obtained from the motor-impaired user is selected from a group consisting of a heart rate, a tone of voice, and a rate of respiration;
map, by the cognitive control system via the at least one processor, each state of the plurality of states to one or more control functions;
select a control function from the one or more control functions based on the determined state of the motor-impaired user; and
adjust, via the selected control function, the scrolling of the visual content outside the viewable display area through the viewable display area on the electronic device to return the determined state of the motor-impaired user to the baseline state, wherein additional biometric data is obtained and processed to determine that the determined state of the motor-impaired user has returned to the baseline state, and wherein the additional biometric data obtained from the motor-impaired user is selected from the group consisting of the heart rate, the tone of voice, and the rate of respiration.

9. The system of claim 8, wherein the viewable display area is determined by calculating a user distance and a viewing angle of the motor-impaired user relative to the display.

10. The system of claim 8, wherein the at least one processor is further configured to continuously modify the one or more control functions to control the scrolling of the visual content based upon real-time or near real-time biometric data obtained from the motor-impaired user.

11. The system of claim 8, wherein the biometric data is obtained from one or more wearable biometric devices.

12. The system of claim 8, wherein the biometric data includes data corresponding to an emotional, psychological, or a physiological state of the motor-impaired user, and wherein a machine learning system maps the biometric data to the determined state of the motor-impaired user.

13. The system of claim 8, wherein the at least one processor is further configured to:
receive a voice instruction from the motor-impaired user; and
move the visual content into the viewable display area based on the voice instruction.

14. A computer program product for providing visual content displayed on an electronic device to a motor-impaired user, the computer program product comprising one or more computer readable storage media collectively having program instructions embodied therewith, the program instructions executable by a processor to:
determine, for the motor-impaired user, a viewable display area on a display of the electronic device, wherein the viewable display area is a fixed area corresponding to a stationary location on the display and wherein the viewable display area is smaller in size than the display;
determine a baseline state of the motor-impaired user;
analyze the visual content to divide into multiple sections comprising key objects;
divide the visual content into the multiple sections;
determine a content navigation path to scroll the multiple sections of the visual content based on a relevance or prominence of each key object of the key objects;
automatically scroll the visual content through the viewable display area according to the determined content navigation path;
obtain biometric data including motor-impaired user data from the motor-impaired user, wherein the biometric data is used by a cognitive control system via the processor to determine a state of the motor-impaired user selected from a plurality of states, the plurality of states corresponding to a stress or interest level of the motor-impaired user, and wherein the biometric data obtained from the motor-impaired user is selected from a group consisting of a heart rate, a tone of voice, and a rate of respiration;
map each state of the plurality of states to one or more control functions;
select a control function from the one or more control functions based on the determined state of the motor-impaired user; and
adjust, via the selected control function, the scrolling of the visual content outside the viewable display area through the viewable display area on the electronic device to return the determined state of the motor-impaired user to the baseline state, wherein additional biometric data is obtained and processed to determine that the determined state of the motor-impaired user has returned to the baseline state, and wherein the additional biometric data obtained from the motor-impaired user is selected from the group consisting of the heart rate, the tone of voice, and the rate of respiration.

15. The computer program product of claim 14, wherein the viewable display area is determined by calculating a user distance and a viewing angle of the motor-impaired user relative to the display.

16. The computer program product of claim 14, wherein the program instructions are executable to continuously modify the one or more control functions to control the scrolling of the visual content based upon real-time or near real-time biometric data obtained from the motor-impaired user.

17. The computer program product of claim 14, wherein the biometric data includes data corresponding to an emotional, psychological, or a physiological state of the motor-impaired user, and wherein a machine learning system maps the biometric data to the determined state of the motor-impaired user.

18. The computer program product of claim 14, wherein the program instructions are executable to: receive a voice instruction from the motor-impaired user; and move the visual content into the viewable display area based on the voice instruction.

19. The computer program product of claim 14, wherein the biometric data is obtained from one or more wearable biometric devices.

\* \* \* \* \*